(12) United States Patent
Kelly et al.

(10) Patent No.: US 7,148,327 B2
(45) Date of Patent: Dec. 12, 2006

(54) PRODUCTION OF SOLUBLE KERATIN DERIVATIES

(75) Inventors: Robert James Kelly, Christchurch (NZ); Gillian Helen Worth, Lincoln (NZ); Alisa Dawn Roddick-Lanzilotta, Christchurch (NZ); Douglas Alexander Rankin, Christchurch (NZ); Gregory David Ellis, Christchurch (NZ); Paul Johannes Roy Mesman, Christchurch (NZ); Conal Garth Summers, Christchurch (NZ); Diane Joyce Singleton, Christchurch (NZ)

(73) Assignee: Keratec Limited, Canterbury (NZ)

( * ) Notice: Subject to any disclaimer, the term of this patent is extended or adjusted under 35 U.S.C. 154(b) by 17 days.

(21) Appl. No.: 10/483,607

(22) PCT Filed: Jul. 17, 2002

(86) PCT No.: PCT/NZ02/00125

§ 371 (c)(1),
(2), (4) Date: Jan. 12, 2004

(87) PCT Pub. No.: WO03/011894

PCT Pub. Date: Feb. 13, 2003

(65) Prior Publication Data

US 2005/0124797 A1 Jun. 9, 2005

(30) Foreign Application Priority Data

Jul. 17, 2001 (NZ) ..................................... 512725

(51) Int. Cl.
*C08H 1/06* (2006.01)
*C07K 1/14* (2006.01)

(52) U.S. Cl. .................................................... 530/357

(58) Field of Classification Search ................ 530/357, 530/350
See application file for complete search history.

(56) References Cited

U.S. PATENT DOCUMENTS

| | | | | |
|---|---|---|---|---|
| 2,591,945 A | * | 4/1952 | Koerner et al. ............. | 530/357 |
| 3,567,363 A | | 3/1971 | Wolfram .................... | 8/127.51 |
| 4,948,876 A | * | 8/1990 | Bore et al. .................. | 530/357 |
| 5,460,967 A | * | 10/1995 | Fink et al. .................. | 435/273 |

FOREIGN PATENT DOCUMENTS

| | | |
|---|---|---|
| FR | 1503640 | 12/1967 |
| GB | 2 115 427 A | 9/1983 |
| WO | WO 99/18922 | 4/1999 |
| WO | WO 00/70049 | * 11/2000 |
| WO | WO 02/09659 A3 | 2/2002 |

OTHER PUBLICATIONS

Harrap et al. Soluble Derivatives of Feather Keratin. The Biochemical Journal. 1986. 8, 5, 258-264.*
Pohl. "Concentration of Proteins and Removal of Solutes" in Methods in Enzymology, 1990, vol. 182, chapt. 7, pp. 68-83.*
McNeil. Heavy metal removal using wool filters. Asian Textile Journal. May-Jun. 2001. vol. 10, 5/6, pp. 88 & 90.*
Fukatsu. Degradation of Fe(III)-wool keratin complex by hydrogen-peroxide. Sen'i Gakkaishi (Fiber), 1990, vol. 46, No. 5, pp. 186-191. Abstract only.*
Swan, J.M., "The Reaction of Protein Thiol and Disulphide Groups with Cupric Sulphite Solutions", Australian Journal of Chemistry., vol. 14, 1960, p. 69-83.
Harrap, B.S., et al., "Soluble Derivatives of Feather Keratin", The Biochemical Journal, vol. 92, No. 1, 1964, p. 8-18.
Mies, Von H.H., et al., "Praparative Gewinnung Ioslicher Proteine aus Wolle", Das Leder, vol. 39, No. 1, 1988, p. 1-9.
Thomas, H., et al., "In Vitro Reconstitution of Wool Intermediate Filaments*", International Journal of Biological Macromolecules, vol. 8, No. 5, 1986, p. 258-264.
Thomas, H., et al., "Versuche zur Isolierung der Matrixproteine von Wolle in der Disulfidform Experiments for the Isolation . . . ", Melliand Textileberichte (Apr. 1983), p. 297-300, w/Eng. translation.

* cited by examiner

*Primary Examiner*—Jon Weber
*Assistant Examiner*—Suzanne M. Noakes
(74) *Attorney, Agent, or Firm*—Bacon & Thomas, PLLC

(57) ABSTRACT

A process for the preparation of soluble proteins of high molecular weight with little or no damage to the structural integrity of the proteins. The process is economically and environmentally acceptable by virtue of the cost of reagents that are used, and the recycling of some of those reagents, and is suitable for the production of soluble proteins on a large scale. The process includes a first stage using oxidative sulfitolysis followed by a second stage using mild conditions to extract the soluble protein. In the case of wool as the protein source the process leads to the production of soluble keratin proteins fractionated into the classes S-sulfonated keratin intermediate filament proteins and S-sulfonated keratin high sulfur proteins.

16 Claims, 1 Drawing Sheet

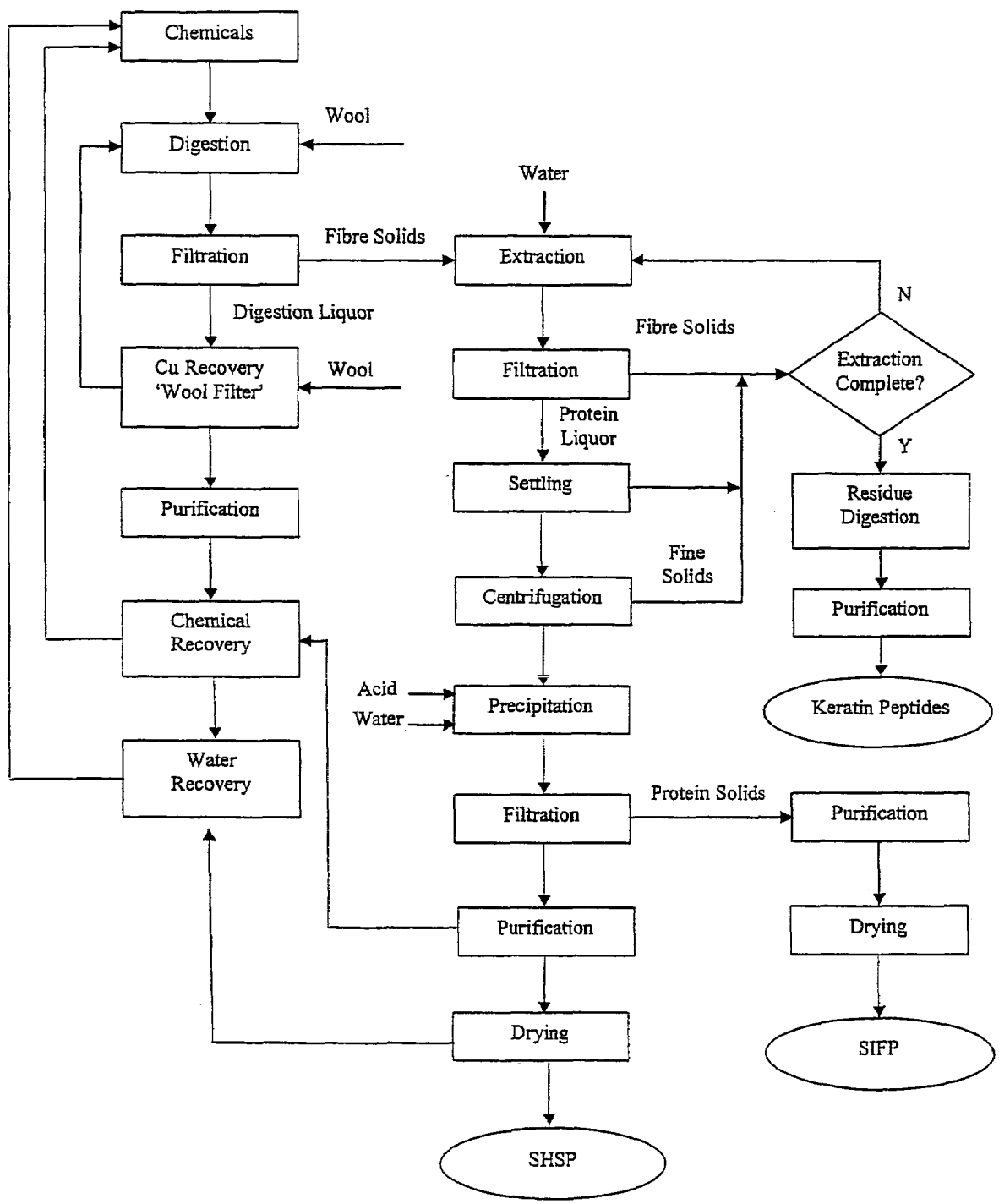
Figure 1: Protein extraction process diagram.

PRODUCTION OF SOLUBLE KERATIN DERIVATIES

FIELD OF THE INVENTION

This invention relates to a process for the preparation of derivatives of keratin from animal sources such as wool, hair, horns, hooves, feathers and scales by an economic and environmentally acceptable process, and to a series of keratin derivative products produced thereby. Some of the keratin derivatives are soluble and can be used in the production of a range of biopolymer materials.

BACKGROUND OF THE INVENTION

Keratins are a class of structural proteins widely represented in biological structures, especially in epithelial tissues of higher vertebrates. Keratins may be divided into two major classes, the soft keratins (occurring in skin and a few other tissues) and the hard keratins, forming the material of nails, claws, hair, horn, feathers and scales.

The toughness and insolubility of hard keratins, which allow them to perform a fundamental structural role in many biological systems, are also desirable characteristics in many of the industrial and consumer materials currently derived from synthetic polymers. In addition to possessing excellent physical properties, keratin, as a protein, is a material with a high degree of chemical functionality and, consequently, exhibits many properties that synthetic materials cannot achieve. Keratin is, therefore, well suited to the development of products with high-value, niche-market applications. Keratin is also an environmentally acceptable polymer produced from a sustainable resource and therefore has environmental benefits over synthetic materials. Following the global trend of developing materials from renewable sources produced in a sustainable process, a range of materials has been produced from keratin, most commonly in the form of keratin films.

At the core of a new industry producing biopolymer materials from keratin it is essential to have a process for extracting keratin from its source that is economically viable, sustainable from an environmental perspective, and produces a stable and versatile product. Methods used to date for the extraction of keratin that maintain the integrity of the individual proteins have been designed for the purpose of protein analysis and characterisation and consequently are not viable on an industrial scale, from an economic and environmental viewpoint. Methods used to date for the economic dissolution of keratin have significantly degrading effects on the protein, and consequently the dissolved protein retains few of the physicochemical properties that lead to the desirability of keratin as a biopolymer, such as the ability to reconstitute into tough materials.

It is an object of the invention to go some way in overcoming the disadvantages with known processes or at least provide the public with a useful choice.

In at least one embodiment the invention strives to provide an economic and environmentally acceptable process for the dissolution of keratin proteins that maintains the structural integrity and chemical functionality of the proteins during the dissolution process and leads to a stable and versatile keratin derivative product for the development of biopolymer materials.

SUMMARY OF THE INVENTION

According to a first aspect the invention provides a dissolution process for producing a range of stable, soluble keratin derivatives of high molecular weight, the molecular weight being similar to or greater than that of proteins originally expressed in the keratin source, with little or no damage to the structural integrity of the constituent proteins. The dissolution occurs in a two-stage process.

According to a preferred aspect the invention provides a process for the preparation of keratin derivatives of high molecular weight, the process including a first stage digestion step of S-sulfonating a keratin source by oxidative sulfitolysis followed by a second stage extraction step using controlled washing with water to thereby obtain a highly S-sulfonated keratin derivative.

The conversion of highly S-sulfonated keratin from a solid state into solution is without the use of chaotropic agents, by controlled, gradual washing of the sulfonated keratin with water in order to wash out the residual chemical reagents from the extraction procedure and alter the ionic strength of the extraction solution.

The first stage involves oxidative sulfitolysis to convert cystine groups present in the protein to S-sulfocysteine, using industrially acceptable concentrations of inexpensive reagents for the purpose of sulfonation (eg. sodium sulfite) and oxidation (eg. cupraammonium hydroxide).

According to another aspect, the invention provides a process for the separation of a gelatinous keratin product from a solution of S-sulfonated keratin produced by the above process, wherein the S-sulfonated keratin derivative solution is treated by the use of a gentle, gravity fed filtration system followed by separation. Preferably the separation is centrifugal.

According to another aspect of the invention, a liquid stream remaining after the gelatinous keratin is removed is processed by passing over scoured wool, thereby removing residual chemicals from the solution and preparing the wool for subsequent protein extraction processes.

Following conversion of the cystine groups, the second stage of the process is one in which the highly S-sulfonted keratin derivative is brought from a solid or gelatinous state into solution by extensive dilution with water. The rate and extent of dissolution can be controlled by the use of heat, surfactants, gentle agitation and vigorous chopping or homogenisation. By controlling the rate of dissolution, reaction solutions can be isolated, for example if a copper oxidant is used a reaction solution rich in copper is produced but it contains little or no dissolved protein, or are rich in protein but contain little or no copper.

According to another aspect of the invention, a liquid stream resulting from the second stage of the process, which contains residual chemicals such as copper sulfate and sulfite, as well as S-sulfonated keratin derivatives, is processed using any one or more of a variety of methods that allow the recycling of reagents from the solution and the separate isolation of purified S-sulfonated Keratin Intermediate Filament Protein(s) (SIFP) and S-sulfonated Keratin High Sulfur Protein(s) (SHSP). This is achieved through the use of chelating agents, such as ethylenediamine tetraacetic acid, or chelating ion exchange resins, such as those containing the iminodiacetic functional group, and the use of isoelectric precipitation to separate protein types. Ultrafiltration can be used at several stages in the process to improve the efficiency of reagent removal or protein separation. Metallic impurities in the protein products can be further reduced by the washing of the protein derivative(s)

following precipitation with dilute acids, water or chelating agents. Once separated, the protein products can be dried by a range of methods such as fluid bed, spray or freeze drying.

Another aspect of the invention is the further processing of residual keratin not dissolved by the two stage sulfitolysis process, through the use of other reagents, such as hydrogen peroxide, sodium sulfide or proteolytic enzymes, to produce keratin peptides.

Another aspect of the invention is the provision of a method for large scale recovery of proteins from a natural source, including subjecting said natural protein source to a treatment sufficient to render at least some of the protein(s) water soluble, and subsequently separating the water soluble protein(s).

Another aspect of the invention is the provision of an installation for large scale recovery of proteins from a natural source, a treatment vessel to contain and subject a large quantity of natural protein source to a treatment sufficient to render at least some of the protein(s) contained in said feed, water soluble, and a separation apparatus to subsequently separate the water soluble protein(s).

Another aspect of the invention is a method of selectively solubilising a protein having plurality of disulfide bonds from a mixture of proteins including subjecting said mixture of proteins to oxidative sulfitolysis to produce a soluble S-sulfonated protein fraction. The oxidative sulfitolysis is preferably effected in the absence of chaotropic agents with little or no damage to the structural integrity of the protein.

Another aspect of the invention is method for obtaining a purified protein from an impure protein source with little or no damage to the structural integrity of the protein including subjecting said protein source to a treatment sufficient to render at least some of the protein(s) water soluble, and subsequently separating the water soluble protein(s) in the absence of chaotropic agents.

BRIEF DESCRIPTION OF THE DRAWINGS

FIG. 1 is a protein extraction process diagram and is referred to below.

DESCRIPTION OF PREFERRED EXAMPLES OF THE INVENTION

The combination of aspects that make up the process as a whole are summarized diagrammatically in attached FIG. 1.

This process method is for the preparation of highly sulfonated keratin derivatives and can be applied to any keratin source, such as animal wool, hair, horns, hooves, feathers or scales. Whilst the application of the method to different keratin sources can give soluble keratins with different structure and properties, the fundamental step of the dissolution process, in which cystine is converted to s-sulfocysteine, applies equally well to all keratin-containing materials.

The process can be conceived as occurring in two stages.

Stage one, which involves the conversion of cystine to S-sulfocysteine, occurs through a procedure of oxidative sulfitolysis. This can be achieved by the use of a sulfonating agent, such as sodium sulfite or sodium metabisulfite, which asymmetrically cleaves the cystine to cysteine and S-sulfocysteine, and an oxidant, which converts the cysteine produced in sulfonation to cystine. By further sulfonation of cystine complete conversion of all cystine to S-sulfocysteine is achieved.

Oxidants which can be used include sodium tetrathionate, iodosobenzoate and cuprammonium hydroxide. In a preferred embodiment of this invention the sulfonating reagent used is sodium sulfite in the concentration range 0.02M to 0.2M and the oxidant used is cuprammonium hydroxide in the concentration range 0.02M to 0.08M, generated by the combination of copper sulfate and ammonia. The first stage of the procedure for solublising keratin is the soaking, for a residence time such as 24 hours, of the keratin source in a solution or sequence of solutions that convert the cystine to S-sulfocysteine, with a liquor to wool ratio (volume:weight) in the range 5:1 to 50:1.

In another embodiment of the invention the sulfonating agent used is sodium metabisulfite in the concentration range 0.1 M to 0.5M, maintained at acidic pH. In this embodiment the wool is removed from the solution containing sodium metabisulfite before being added to a solution containing a cuprammonium complex in the concentration range 0.02M to 0.08M.

Previous work relating to the use of the oxidative sulfitolysis procedure has required the use of large concentrations of chaotropic agents, such as urea or guanidinium hydrochloride, in order to swell the keratin source and facilitate the dissolution of keratin. This procedure is both expensive and impractical on an industrial scale. Previous work relating to the use of oxidative sulfitolysis using copper as the oxidant has been conducted under conditions of temperature and pH that are detrimental to the integrity of the protein causing high rates of conversion of cystine to lanthionine.

Stage two of the process involves the conversion of highly sulfonated keratin from a solid state into solution without the use of chaotropic agents and under conditions of temperature and pH that maintain the structural integrity of the protein, by controlled, gradual washing of the sulfonated keratin with water in order to wash out the residual chemical reagents from the extraction procedure and alter the ionic strength of the extraction solution. This combination of effects results in the conversion of the highly sulfonated keratin from the solid state into aqueous solution. In the preferred procedure the reaction volume is replaced every 12 to 48 hours, either in a batch process or on a continuous basis.

The rate and extent of dissolution can be controlled by the use of surfactants, the action of heat, agitation, and homogenisation of the sulfonated keratin. A feature of the invention is to use these factors to control the rate of extraction. The highly S-sulfonated keratin can, therefore, be kept in the solid state and separated from the extraction solution containing the bulk of the chemicals used for the sulfonation process. The preferred procedure uses a non-ionic surfactant, such as Triton X 100 in the range 0.1% to 5% by weight, and a temperature maintained in the range 15° C. to 50° C.

An advantage of the invention when a copper based oxidant is used is the re-use of this copper-rich extraction solution for subsequent extraction processes, significantly reducing both the cost and environmental impact of the process. Re-use of the copper-rich solution is possible due, in part, to the regeneration of the active copper species through aerial oxidation. One method in which the copper-rich solution can be efficiently reused is by passing the solution over wool. Wool binds copper from the solution, and if this wool is then used for subsequent extraction processes, the demand for copper in those subsequent extractions is reduced. In this way, a 'wool filter' can be used as a key step in the processing of the copper-rich extraction solution, reducing the subsequent need for effluent treatment and also the need for copper to be added to the subsequent processes. In a typical procedure the liquid stream from stage 1 contained approximately 1800–1500 (parts per million) ppm copper, and after passing over the wool filter this was reduced to approximately 400–300ppm.

The first stage of the process, and the recovery of reagents for use in the process are indicated in the attached FIG. 1.

After S-sulfonation and homogenisation the keratin material becomes a gelatinous swollen fibrous mass.

A further advantage of the invention is the separation of the highly S-sulfonated keratin derivatives in the solid state from solutions containing either chemicals used in the extraction process or the keratin protein in solution. This separation is effectively achieved by the use of a gentle, gravity based filtration through a fine mesh screen, followed by centrifugal separation of the filtrate from fine particulates.

Solutions of highly S-sulfonated keratin derivatives can be purified with regard to metal ions, specifically the copper ions used as part of the extraction process, through the use of ion exchange media, in particular those containing iminodiacetic acid functionality known to possess a high affinity for divalent metal ions. This ion exchange medium may be present in the form of a packed resin column, over which the protein solution is passed, or it may alternatively form part of an electrochemical cell, in which copper is recovered from the ion exchange medium through the use of an applied voltage and a system containing permeable membranes.

Once the highly S-sulfonated keratin derivates are in solution particular proteins eg. the S-sulfonated keratin intermediate filament protein can be readily isolated by isoelectric precipitation, around pH 4 or below, using acids such as sulfuric acid, hydrochloric acid, citric acid or acetic acid, with the preferred procedure using sulfuric acid. An advantage of the invention is the minimisation of the binding of copper and other metallic impurities to the protein prior to isoelectric precipitation through the use of ion exchange media as described, or by addition of a chelating agent, such as ethylenediaminetetraacetic acid (EDTA), to the protein solution. In the preferred example EDTA (0.2M) is added to the liquid stream from stage 2 at a rate of 25 ml per liter, or at a rate suitable to sequester all the copper ions present in solution as indicated by analysis of the solution. Metallic impurities can be further reduced by the washing of the protein, once isolated by precipitation, with a dilute acid solution, or solution of a chelating agent such as EDTA, or water.

Following precipitation and washing the separated protein can be isolated in a stable, dry state using drying methods involving air flows at about ambient temperature, for example with the use of a fluid bed dryer. Alternatively, the product can be dried using a freeze dryer. The dry protein product contains cystine groups in the form of S-sulfonic acid and consequently the protein is only soluble in the presence of a base, such as sodium hydroxide or ammonium hydroxide. These processes are represented as drying in the attached FIG. 1.

The highly soluble keratin derivatives that remain in solution following isoelectric precipitation, which in the case of wool are mainly the high sulfur matrix proteins from within the wool fibre, can be isolated in a stable form from solution through a process of ultrafiltration, to remove non-proteinacious species such as residual copper or EDTA, followed by spray drying.

A feature of the invention is the use of a combination of isoelectric precipitation and ultrafiltration followed by spray drying to separate highly S-sulfonated keratins according to their properties in solution. In the case of wool keratin, this effectively separates the low sulfur intermediate filament protein class from the high sulfur matrix protein class and provides two product streams with different chemical properties.

A feature of the invention is the preparation of a stable, water soluble form of the highly S-sulfonated keratin derivative, by dissolving the S-sulfonic acid form of keratin in the presence of base and spray drying the resulting solution.

A feature of the invention is the combination of engineering components to allow solublisation of the keratin and isolation of the S-sulfonated keratin from solution in a continuous, semi-continuous, or batch process. This combination of engineering components and unit operations is detailed in FIG. 1.

An advantage of the invention is the recovery and reuse of copper from the reaction mixtures and effluent streams of the process. Copper can be recovered using electrochemical methods, including the use of selective permeable membranes in order to separate copper ions from EDTA prior to electrochemical deposition. Alternatively, immobilized binding agents, in the form of copper-specific ion exchange resins, can be used to remove copper from the effluent stream. Copper removed using these methods can be reused, thereby minimizing the environmental impact of the process.

The use of ion exchange media and/or chelating agents is represented as purification in the attached FIG. 1.

Another advantage of the invention is the further processing of residual keratin which remains in the solid state following the extraction procedure. This functionalised keratin is highly S-sulfonated, therefore the disulfide bonds present in the native keratin that render it resistant to chemical and enzymatic attack have been cleaved and the keratin is readily digestible using other extraction methods. For example, a solution rich in keratin peptides can be prepared through the action on this residual keratin of alkaline solutions of a strong oxidant such as hydrogen peroxide, in the concentration range 10–100 ml of 50% hydrogen peroxide per kg of the keratin residue under alkaline conditions. The keratin residue contains approximately 5% solids. Alternatively, solutions of strong reductants such as sodium sulphide in the concentration range 0.5%–15% added to the keratin residue can be used to prepare a solution rich in keratin peptides. Alternatively, proteolytic enzymes, such as those of the subtilisin, papain or trypsin groups, can be employed at levels in the range 0.1 mg–20 mg of enzyme per gram of keratin residue at temperature and pH conditions appropriate for the specific enzyme to readily digest the residual keratin and prepare a solution rich in keratin peptides. All of these methods result in the formation of a solution rich in keratin peptides which can be processed in a similar manner to the liquid stream resulting from stage 2 described above, that is through the use of ion exchange media, pH adjustment and drying (shown as purification and drying in FIG. 1), to produce keratin peptide solids. Digestion of the keratin residue in this way minimises the keratin waste produced by the process as a whole, and ensures maximum utility of the keratin protein present in the keratin source.

The two intact protein products from the process are S-sulfonated keratin intermediate filament protein and S-sulfonated keratin high sulfur protein. The S-sulfonated keratin intermediate filament protein typically produced by the process was analysed using sodium dodecylsulfate polyacrylamide gel electrophoresis (SDS-PAGE) analysis using a reduction/alkylation procedure, which indicated a molecular weight distribution predominantly in the range 30–60 kD (intermediate filament proteins), with a small component of protein of mass 10 kD (high glycine high tyrosine proteins). The amino acid composition of this product is given in Table 1 and is typical for wool keratin intermediate filament proteins. The S-sulfonated keratin high sulfur protein was analysed using SDS-PAGE after a reduction/alkylation procedure, which indicated a molecular weight predominantly in the range 15–20 kD. The amino acid composition of this product is given in Table 1 and is typical for wool keratin high sulfur proteins.

Example 1b

Stage 1, Digestion with the Use of Surfactant

In a variation of example 1a, the digestion solution was prepared with the addition of 1% of a non-ionic surfactant Triton X 100. The addition of this surfactant resulted in a delay in the release of soluble protein from the fibre, allowing a more effective separation of protein from residual reagents such as copper salts in the extraction solution.

TABLE 1 amino acid composition of S-sulfonated keratin intermediate filament protein (STEP), S-suffonated keratin high sulfur protein (SHSP), intermediate filament protein (IFP) and high sulfur protein (HSP) (later two courtesy of Gillespie and Marshall, Variability in the proteins of wool and hair, Proc. Sixth Int. Wool Text. Res. Conf, Pretoria, 2, 67–77, 1980). All residues expressed as mol %. S-sulfocysteine, cystine and cysteine are measured as S-carboxymethyl cysteine following reduction and alkylation.

|  | Cya | Asp | Glu | Ser | Gly | His | Arg | Thr | Ala | Pro | Tyr | Val | Met | Lan | Ile | Leu | Phe | Lys | Cys |
|---|---|---|---|---|---|---|---|---|---|---|---|---|---|---|---|---|---|---|---|
| SIFP | 0.4 | 7.9 | 15.4 | 10.9 | 8.1 | 0.9 | 7.9 | 6.5 | 7.5 | 5.4 | 1.1 | 6.5 | 0.2 | 0.2 | 3.7 | 8.9 | 2.5 | 2.1 | 4.2 |
| SHSP | 1.7 | 2.6 | 8.6 | 14.3 | 9.1 | 0.8 | 6.8 | 10.4 | 3.6 | 12.6 | 1.8 | 6.3 | 0.0 | 0.2 | 2.9 | 3.9 | 1.5 | 0.4 | 12.4 |
| IFP | 0.0 | 9.6 | 16.9 | 8.1 | 5.2 | 0.6 | 7.9 | 4.8 | 7.7 | 3.3 | 2.7 | 6.4 | 0.6 | 0.0 | 3.8 | 10.2 | 2.0 | 4.1 | 6.0 |
| HSP | 0.0 | 2.3 | 7.9 | 13.2 | 6.2 | 0.7 | 6.2 | 10.2 | 2.9 | 12.6 | 2.1 | 5.3 | 0.0 | 0.0 | 2.6 | 3.4 | 1.6 | 0.6 | 22.1 |

An example of the process is shown diagrammatically in the attached FIG. 1. Ultrafiltration is considered as being a possible component in each purification stage. The key components are illustrated by the following examples of a protein extraction procedure.

EXAMPLES

Example 1

Stage 1, Digestion

The digestion stage of the process involves the use of oxidative sulfitolysis to convert cystine to S-sulfocysteine within the keratin source.

Example 1a

Stage 1, Digestion

In order to extract the keratin from 10 kg of wool, firstly 2 kg of copper sulfate pentahydrate was mixed using a high shear mixer with eight litres of concentrated ammonia. This mixture was diluted to 200 L with water and 10 kg of wool was added. Approximately 15 L of sulfuric acid (2M) was-added to the stirred mixture till a pH 9.4 was achieved. Anhydrous sodium sulfite (5.04 kg) was added and the solution mixed until complete dissolution of all of the reagents had occurred and the pH stabilised at 9.5. The final concentration of the cupric ammonia complex was 0.04M. The sodium sulfite had a final concentration of 0.2M. The temperature of the digestion solution was maintained at 20° C. After 24 hours of gentle agitation the fibrous gelatinous mass of softened wool was filtered. The filtrate was passed through a fresh wool filter, which decreased the copper level in the solution from 1725 ppm to 130 ppm, and further purified using Purolite S930 IDA ion exchange resin, which under acidic conditions further reduced the copper level to 12 ppm. Fresh water was added to the softened wool and the mixture was agitated.

Example 1c

Stage 1, Digestion

In a variation of example 1a, the digestion stage occurs in two parts. In the first part wool is pretreated with sodium metabisulfite at a concentration of 0.2M, at pH 4.2. Following removal of the wool from this solution, and with no attempt to remove residual sulfite from the wool, the wool was immersed in a cuprammonium hydroxide solution, at the concentration and pH described in example 1a for a further 24 hours at 20° C.

Example 2

Stage 2, Extraction

Example 2a

Stage 2, Batch Extraction

Following completion of stage 1, described in examples 1, the mixture was agitated for a period of 16 hours, before being homogenized. Following a further 4 hours of agitation the solids and solution were separated using a two-stage filtration process involving a wedge wire screen followed by a settling tank and a spinning disc centrifuge. The solid phases were returned to the reaction vessel and water was added to give a final liquor to wool ratio of 20:1 based on original wool solids. Following 24 hours agitation or continuous homogenisation the mixture was separated by repeating the two-stage filtration process. The solid phases were returned to the extraction vessel and further diluted. This cycle was repeated 7 to 12 times. The liquid phases, containing soluble proteins, were further processed as detailed below in example 3.

Example 2b

Stage 2, Continuous Extraction

Following completion of stage 1 the mixture was processed as described in example 2a, except that the two stage filtration process occurred on a continuous process, and solids and fresh water were added to the reaction tank at a rate equivalent to the volume of the tank being replaced in 24 hours. This process was continued for 120 hours.

Example 3

Processing of Protein Solutions

Ultrafiltration can be used at several points during the processing of protein solutions, in order to concentrate solutions and make the processes of drying and ion exchange more efficient. Ultrafiltration may be used prior to any processing step outlined in the following examples.

Example 3a

Processing of Protein Solutions Using EDTA

The solution produced as a result of stage 2, as described in Example 2, was further processed to isolate purified soluble keratins. EDTA (0.2M) was added to the liquid phase at a rate of 25 mL per liter, or at a rate suitable to sequester all the copper ions present in solution as indicated by analysis of the solution. Following 1 hour of mixing, the pH of the filtrate was reduced to 3.5 using sulfuric acid. The protein precipitate was isolated using a screen, and washed sequentially with dilute sulfuric acid and water. The protein, S-sulfonated keratin intermediate filament protein, was dried by one of three routes, freeze drying, fluid bed drying or spray drying following dissolution with dilute sodium hydroxide. The filtrate following the protein precipitation procedure was further processed using ultrafiltration, to separate the protein components from the residual reagents. The retentate was spray dried to isolate further soluble protein, S-sulfonated keratin high sulfur protein. The permeate was further processed to recover copper and EDTA from the effluent stream using ion exchange media.

Example 3b

Processing of Protein Solution Using Ion Exchange Media

The solution produced as a result of stage 2, as described in Example 2, was further processed to isolate purified soluble keratins. The liquid phase was passed over ion exchange resin, such as the chelating resin Purolite S930 IDA ion exchange resin containing the iminodiacetic acid functional group, in order to remove copper ions from the solution. Following ion exchange the pH of the filtrate was reduced to 3.5 using sulfuric acid and further processed in an identical manner to that described for Example 3a.

3c. Processing of Protein Solution Using pH Adjustment Prior to Ion Exchange.

The solution produced as a result of stage 2, as described in example 2, was further processed to isolate purified soluble keratins. The pH of the liquid phase was reduced to 3.5 using sulfuric acid. The protein precipitate was isolated using a screen, redissolved using dilute sodium hydroxide and further purified with either the addition of EDTA or by passing over an ion exchange column. Following further purification, the pH of the solution was reduced to 3.5 using sulfuric acid and the protein was isolated as described in the earlier examples. The filtrate from the initial pH reduction step, which still contains significant amounts of soluble protein and other reagents, was purified by passing over ion exchange media and spray dried to isolate further soluble protein, S-sulfonated keratin high sulfur protein.

Example 4

Dissolution of Residues from Stage 2

The solid stream isolated as a result of stage 2 can be further processed to produce keratin peptides by a range of methods. The high level of sulfonation of the residue makes it readily amenable to chemical and enzymatic digestion, as the disulfide bonds present in the original keratin source resistive to chemical and enzymatic attack have largely been cleaved.

Example 4a

Dissolution of Residues Using Sodium Sulfide

Sodium sulfide solution (5% by weight) is added to an equal volume of the solid stream from stage 2 of the process, which comprises approximately 5% solids. The mixture is agitated for 12 hours after which time the solids are removed by filtering and centrifugation and sulfuric acid is added to the protein solution to decrease the pH to the range 2 to 3.5. The precipitate is collected on a screen and washed thoroughly with water.

Example 4b

Dissolution of Residues Using Hydrogen Peroxide

Hydrogen peroxide (50%) is added to the solid stream from stage 2 at a level of 25–30 ml per kg of keratin residue (keratin residue contains approximately 5% solids). This is mixed and 1 M sodium hydroxide is added to obtain pH in the range of 10 to 13. The mixture is agitated gently for 24 hours and the protein and solids separated by the two stage filtration process described in Example 2 and protein isolated by acidification as described in Example 4a. Alternatively the protein solution is passed over an ion exchange resin, then acidified and the precipitated solid collected. The acidified solution may then be passed through an ion exchange column prior to freeze-drying or spray drying to collect a further protein-rich product.

4c Dissolution of Residues Using Proteolytic Enzymes

An industrial subtilisin enzyme preparation (a solution containing 2.5% active enzyme) was added to the solid stream from stage 2 in the amount of 10 mg of active enzyme per gram of keratin residue. The pH was maintained at 9.5 with the addition of sodium hydroxide and the reaction heated to 60° C. for 2 hours. The resulting protein solution is isolated from solids and processed as described in 4a or passed through ion-exchange resin prior to and/or following acidification as described in 4b.

Thus by the invention there is provided a method for the production of soluble keratin derivatives that is both economic and environmentally acceptable.

Particular examples of the invention have been described and it is envisaged that improvements and modifications can take place without departing from the scope of the attached claims.

The invention claimed is:

1. A process for preparing S-sulfonated keratin protein comprising the steps of:
   (a) reacting a keratin source with oxidative sulfitolysis to produce solids comprising reaction product in digestion liquor,
   (b) separating the solids from the digestion liquor,
   (c) extracting the solids with a composition consisting of water or water and surfactant and separating extract from solids, where the extraction can be repetitive or continuous, and
   (d) processing extract to recover S-sulfonated keratin protein.

2. The process of claim 1 where the keratin source is wool.

3. The process of claim 1 where the post-extract solids of step (c) comprise water insoluble gelatinous composition.

4. The process of claim 1 where the digestion liquor includes copper containing reactant.

5. The process of claim 4 where the oxidative sulfitolysis provides metal ions which remain in the extract and the processing of step (d) comprises sequestering the metal ions in the extract with a chelating agent.

6. The process of claim 5 where the chelating agent is EDTA.

7. The process of claim 1, where step (b) is performed by filtration.

8. The process of claim 1, where the separation of extract from solids in step (c) is performed by filtration.

9. The process of claim 1, where oxidative sulfitolysis provides metal ions which remain in the extract and the S-sulfonated keratin protein comprises S-sulfonated high sulfur keratin protein and S-sulfonated intermediate filament keratin protein.

10. The process of claim 1, where step (a) is performed without the use of a chaotropic agent.

11. The process of claim 1, where step (a) is performed under conditions of pH that maintain the integrity of the protein.

12. The process of claim 1, where the keratin source is wool.

13. A process for preparing S-sulfonated high sulfur keratin protein from S-sulfonated keratin protein comprising the steps of:
   (a) reacting a keratin source with metal ion containing oxidative sulfitolysis to produce solids comprising reaction product in digestion liquor, wherein said metal ions remain in the extract,
   (b) separating the solids from the digestion liquor,
   (c) extracting the solids, either repetitively or continuously, with a composition consisting of water or water and surfactant and separating the extract from the solids, wherein said solids comprise a water insoluble gelatinous composition,
   (d) processing the extract to recover the soluble keratin proteins,
   (e) adding acid and water to the extract to precipitate the S-sulfonated keratin intermediate filaments protein
   (f) filtering the precipitate to produce a filtrate containing the S-sulfonated high sulfur keratin protein,
   (g) ultrafiltering the filtrate and recovering the retentate,
   (h) drying the retentate to produce purified S-sulfonated high sulfur keratin protein.

14. A process for preparing S-sulfonated intermediate filament keratin protein from S-sulfonated keratin protein comprising the steps of:
   (a) reacting a keratin source with metal ion containing oxidative sulfitolysis to produce solids comprising reaction product in digestion liquor, wherein said metal ions remain in the extract,
   (b) separating the solids from the digestion liquor,
   (c) extracting the solids, either repetitively or continuously, with a composition consisting of water or water and surfactant and separating the extract from the solids, wherein said solids comprise a water insoluble gelatinous composition,
   (d) processing the extract to recover the soluble keratin proteins,
   (e) adding acid and water to the extract to precipitate the S-sulfonated intermediate filament keratin protein,
   (f) filtering the S-sulfonated intermediate filament keratin protein and recovering the solids,
   (g) drying the solids to produce purified S-sulfonated intermediate filament keratin protein.

15. A process for preparing soluble keratin peptides from S-sulfonated keratin protein comprising the steps of:
   (a) reacting a keratin source with oxidative sulfitolysis to produce solids comprising reaction product in digestion liquor,
   (b) separating the solids from the digestion liquor,
   (c) extracting the solids, either repetitively or continuously, with a composition consisting of water or water and surfactant and separating the extract from the solids, wherein said solids comprise a water insoluble gelatinous composition,
   (d) contacting the insoluble gelatinous composition of (c) with an agent selected from the group consisting of sodium sulfide solution, hydrogen peroxide solution in the presence of residual metal ions and proteolytic enzymes to produce soluble keratin peptides containing solution, and
   (e) processing the solution of (d) to recover the soluble keratin peptides.

16. The process of claim 15, wherein the proteolytic enzyme is from the subtilisin, papain or trypsin family.

* * * * *